United States Patent
Park et al.

(10) Patent No.: US 8,900,586 B2
(45) Date of Patent: Dec. 2, 2014

(54) ANTIBODY THAT BINDS DOMAIN 2 OF ICAM-1 AND METHODS OF TREATMENT

(75) Inventors: Seong Hoe Park, Seoul (KR); Kyeong Cheon Jung, Seoul (KR)

(73) Assignees: Dinona Inc., Seoul (KR); SNU R&DB Foundation, Seoul (KR)

( * ) Notice: Subject to any disclaimer, the term of this patent is extended or adjusted under 35 U.S.C. 154(b) by 0 days.

(21) Appl. No.: 14/128,815

(22) PCT Filed: Jul. 5, 2011

(86) PCT No.: PCT/KR2011/004908
§ 371 (c)(1),
(2), (4) Date: Feb. 14, 2014

(87) PCT Pub. No.: WO2013/005873
PCT Pub. Date: Jan. 10, 2013

(65) Prior Publication Data
US 2014/0148583 A1 May 29, 2014

(51) Int. Cl.
*A61K 39/395* (2006.01)
*C07K 16/28* (2006.01)
*C12N 5/12* (2006.01)
*C07K 16/00* (2006.01)
*C12N 5/16* (2006.01)

(52) U.S. Cl.
CPC .............. *C07K 16/00* (2013.01); *C07K 16/2821* (2013.01); *C12N 5/163* (2013.01)
USPC .................. 424/143.1; 424/130.1; 424/133.1; 424/141.1; 424/152.1; 424/172.1; 435/326; 435/332; 530/387.1; 530/387.3; 530/388.1; 530/388.2; 530/388.22

(58) Field of Classification Search
None
See application file for complete search history.

(56) References Cited

U.S. PATENT DOCUMENTS

2010/0168394 A1    7/2010    Park et al.

OTHER PUBLICATIONS

Schroeder et al., J. Surg. Res. 111:109-119 (2003).*
Auchincloss in Transplantation Immunology, Bach and Auchincloss, Eds., Wiley-Liss, New York, 1995; see Chapter 11, pp. 211-218.*
Jacques Banchereau & Ralph M. Steinman, "Dendritic cells and the control of immunity" Nature. 1998, 392: 245-252 (Mar. 19, 1998).
Sergio Rutella, Silvio Danese and Giuseppe Leone, "Tolerogenic dendritic cells: cytokine modulation comes of age" Blood. 2006, vol. 108, No. 5:1435-1440 (Sep. 1, 2006).
Donald E. Staunton et al., "The Arrangement of the Immunoglobulin-like Domains of ICAM-I gnd the Binding Sites for LFA-1 and Rhinovirus" Cell, vol. 61, 243-254, (Apr. 20, 1990).
Andrew W. Boyd et al., "Intercellular adhesion molecule 1 (ICAM-1) has a central role in cell-cell contact-mediated immune mechanisms" Proc. Nati. Acad. Sci. USA vol. 85, pp. 3095-3099, Immunology (May 1988).
A. Benedict Cosimi et al., "In Vivo Effects of Monoclonal Antibody to ICAM-1 (CD54) in Nonhuman Primates with Renal Allografts" Thej Ournaloafl iM Munology, Voi. 144.4604-4612, No. 12. (Jun. 15, 1990).
Arthur F. Kavanaugh et al., "Treatment of Refractory Rheaumatoid Arthritis with a Monoclonal Antibody to Intercellular Adhesion Molecule 1" Arthritis & Rheumatism vol. 37, No. 7, pp. 992-999, (Jul. 1994).
Arthur F. Kavanaugh et al., "A Phase I/II Open Label Study of the Safety and Efficacy of an Anti-ICAM-1 (Intercellular Adhesion Molecule-1; CD54) Monoclonal Antibody in Early Rheumatoid Arthritis" J Rheumatol., 23:1338-1344 (Aug. 1996).
Salmela, Kaija et al., "A Randomized Multicenter Trial of the Anti-ICAM-1 Monoclonal Antibody (Enlimomab) for the Prevention of Acute Rejection and Delayed Onset of Graft Function in Cadaveric Renal Transplantation: A Report of the European Anti-ICAM-1 Renal Transplant Study Group" Transplantation, Issue: vol. 67(5), pp. 729-736, (Mar. 15, 1999).
Enlimomab Acute Stroke Trial Investigators, "Use of anti-ICAM-1 therapy in ischemic stroke Results of the Enlimomab Acute Stroke Trial" Neurology 57: 1428-1434 (Oct. 2001).
Juha Vuorte et al, "Anti-ICAM-1 Monoclonal Antibody R6.5 (Enlimomab) Promotes Activation of Neutrophils in Whole Blood1" The Journal of Immunology; 162: 2353-2357 (Feb. 1999).
Grochowiecki, T. et al, 'Induction of unresponsiveness to islet xenograft by MMC treatment of graft and blockage of LFA-1/ICAM-1 pathway', Transplantation, vol. 69, No. 8, pp. 1567-1571 (Apr. 27, 2000).
Wong, J. et al, 'Role of ICAM-1 in chronic hepatic allograft rejection in the rat', Ammerican Journal of Physiology-Gastrointestinal and Liver Physiology, vol. 283, pp. G196-G203 (Feb. 20, 2002).
Narang, A.S. and Mahato, R.I., 'Biological biomaterial approaches for improved islet transplantation', Pharmacological Review, vol. 58, No. 2, pp. 194-243 (Jun. 2006).
Rayat, G.R.and Gill, R.G.,'Indefinite survival of neonatal porcine islet xenografts by simultaneous targeting of LFA-1 and CD154 or CD45RB', Diabetes, vol. 54, pp. 443-451 (Feb. 2005).

\* cited by examiner

*Primary Examiner* — Phillip Gambel
(74) *Attorney, Agent, or Firm* — Lexyoume IP Meister, PLLC (57) ABSTRACT

The present invention relates to an antibody binding to the domain 2 of human intercellular adhesion molecules-1 (ICAM-1) where the antibody is able to modulate the differentiation status of dendritic cells and induce antigen-specific T cell tolerance, thereby be effective in the prevention and/or treatment of T cell-mediated immune disorders such as transplantation rejection, graft-versus-host disease, and autoimmune disease. In addition, the present invention provides a pharmaceutical composition comprising the antibody, and method of using them for the treatment of disease.

22 Claims, 7 Drawing Sheets

ANTIBODY THAT BINDS DOMAIN 2 OF ICAM-1 AND METHODS OF TREATMENT

FIELD OF THE INVENTION

The present invention relates to an antibody binding to human intercellular adhesion molecules-1 (ICAM-1) where the antibody is able to modulate the differentiation and function of dendritic cells and prolong the graft survival. In addition, the present invention provides a pharmaceutical composition comprising the antibody, and method of treating immune disorders using them.

BACKGROUND OF INVENTION

Dendritic cells (DCs) are highly specialized antigen-presenting cells that integrate a variety of immune response (Nature. 1998, 392:245-252), and include a heterogeneous family of professional antigen presenting cells involved in initiation of immunity and immunologic tolerance. Until now, immature DCs were believed to induce T-cell anergy, whereas DCs transformed into mature DCs by activation stimuli such as lipopolysaccharide (LPS) were thought to induce primary T cell response (Blood. 2006, 108:1435-1440). Furthermore, semimature DCs with a distinctive cytokine production profile might be endowed with tolerogenic functions (Blood. 2006, 108:1435-1440).

ICAM-1 is a 90 kDa type I cell surface glycoprotein composed of five extracellular immunoglobulin superfamily domains (Cell. 1990, 61:243-54). ICAM-1 mediates leukocyte/leukocyte interaction such as interaction between T cells and antigen presenting cells. It also mediates leukocyte extravasation into tissue during inflammatory processes (Transplantation. 1999, 67:729-736). In vitro study showed that antibodies interfering the ICAM-1/leukocyte function antigen-1 (LFA-1) interaction are able to inhibit T cell adhesion to endothelial cells and T cell activation also could be significantly reduced in a mixed lymphocyte reaction by these antibodies (Proc Natl Acad Sci USA. 1988, 85:3095-3099). In monkey studies using a murine monoclonal antibody, R6-5-D6 (enlimomab), which binds the domain of human ICAM-1, renal allograft survival has been prolonged and T cell infiltration in the graft was decreased compared with controls (J Immunol. 1990, 144:4604-4612). Enlimomab also had been proved to be beneficial in depressing disease activity in patient with rheumatoid arthritis (Arthritis Rheum. 1994, 37:992-999; J Rheumatol. 1996, 23:1338-1344). However, enlimomab induction therapy after renal transplantation in a randomized multicenter study was not able to reduce the rate of acute rejection or the risk of delayed onset of graft function (Transplantation. 1999, 67:729-736). Moreover, clinical trial in acute ischemic stroke patient revealed that anti-ICAM-1 therapy with enlimomab was not an effective and indeed significantly worsen stroke outcome and induced more adverse effect, primarily infections and fever compared with placebo (Neurology. 2001, 57:1428-1434). The enlimomab functions by blocking the adhesion of T cells as wells as neutrophils to the vascular endothelial cells and thus it has been suggested that interfering with neutrophil emigration potentially increases the susceptibility to infection (J Immunol. 1999, 162:2353-2357).

Another anti-ICAM-1 monoclonal antibody, MD-3, has been known to suppress transplantation rejection (US Patent Publication No. 2010-0168394-A1). Unlike R6-5-D6, this antibody binds the domain of ICAM-1 and does not block the interaction between ICAM-1 and LFA-1. Rather then, this antibody suppresses T cell function via modulating the development and function of dendritic cells.

SUMMARY OF THE INVENTION

An embodiment of the present invention relates to an antibody binding to the domain 2 of human intercellular adhesion molecules-1 (ICAM-1) where the antibody is able to modulate the differentiation and function of dendritic cells and induce antigen-specific T cell tolerance, thereby being effective in the prevention and/or treatment of T cell-mediated immune disorders, such as transplantation rejection, graft-versus-host disease, and autoimmune disease. In addition, the present invention provides a pharmaceutical composition comprising the antibody. The present invention further provides a pharmaceutical composition comprising the antibody for treating the T cell-mediated immune disorders, the antibody for use in treating the T cell-mediated immune disorders, and a method of treating the T cell-mediated immune disorders using the antibody.

More particularly, the present invention relates to anti-human ICAM-1 antibody that modulates the differentiation and functions of dendritic cells via binding domain 2 of human ICAM-1, and induces antigen-specific T cell tolerance rather than generalized suppression of immune function. Thereby, the administration of this antibody could be effective in the prevention and/or treatment of T cell-mediated immune disorders, such as transplantation rejection, graft-versus-host disease, autoimmune disease, and the like, while it minimize the adverse effects by immunosuppression, such as infection and development of cancer.

The invention is further relates to a method for producing the antibody, and a cell producing the antibody or its fragment. The invention also includes the hybridoma cell for producing the antibody, and the antibody produced by the hybridoma cell.

The present invention also relates to a pharmaceutical composition for the prevention and/or treatment of T cell-mediated immune disorders, such as transplantation rejection, graft-versus-host disease, autoimmune disease, and the like. The pharmaceutical composition is comprised of an immunosuppressive agent selected from the group consisting of: an antibody capable of binding the domain 2 of ICAM-1 and inducing antigen-specific T cell tolerance, where the antibody is preferably produced by the hybridoma; and a fragment of the antibody, the fragment being capable of binding the domain 2 of ICAM-1 and inducing antigen-specific T cell tolerance.

Further, the present invention also relates to a method for the prevention and/or treatment of T cell-mediated immune disorders, such as transplantation rejection, graft-versus-host disease, autoimmune disease and the like, which comprises administering one or more selected from the group consisting of the antibody or the fragment of the antibody to a patient in need thereof. The antibody or the fragment of the antibody is preferably selected from the group consisting of monoclonal antibodies, and more preferably it is originated from human and animal.

Further, the present invention further relates to an antibody capable of binding the domain 2 of ICAM-1 and inducing antigen-specific T cell tolerance, where the antibody is preferably produced by the hybridoma, and a fragment of the antibody, being capable of binding the domain 2 of ICAM-1 and inducing antigen-specific T cell tolerance, for use in preventing and/or treating T cell-mediated immune disorders, such as transplantation rejection, graft-versus-host disease, autoimmune disease, and the like.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing, wherein.

DETAILED DESCRIPTION

The present invention is further explained in more detail with reference to the following examples. These examples, however, should not be interpreted as limiting the scope of the present invention in any manner.

The present invention relates to a mouse anti-human ICAM-1 monoclonal antibody, designated MD-3 (for example, produced by a hybridoma cell deposited as accession number of KCLRF-BP-00264), fragments of MD-3, and a chimeric or humanized form of MD-3 capable of inducing T cell tolerance. More particularly, the present invention relates to an anti-human ICAM-1 antibody produced by a hybridoma cell deposited as accession number of KCLRF-BP-00264 that modulates the differentiation and function of dendritic cells via binding domain 2 of human ICAM-1 and induces antigen-specific T cell tolerance rather than generalized suppression of immune function. Thereby, the administration of this antibody could be effective in the prevention and/or treatment of T cell-mediated immune disorders, such as transplantation rejection, graft-versus-host disease, and autoimmune disease, while it minimize the adverse effects by immunosuppression, such as infection and development of cancer.

The invention is further directed a method for producing the antibody or its fragment. The method of producing the antibody or its fragment includes the step of (a) immunization an animal with human ICAM-1 protein (Gene Bank Accession No. NP_000192) or protein fragments or a cell expressing human ICAM-1, such as activated human peripheral blood mononuclear cells and/or DU 145 (ATCC HTB-81), (b) extracting splenocytes from the immunized animal, (c) fusing the spleen cells of the animal with a myeloma cell line, and (d) screening the hybridoma cells and selecting the desired hybridoma cells that is capable of modulating the differentiation and function of dendritic cells as wells as suppressing the rejection of transplanted organs but not inhibiting the interaction between ICAM-1 and LFA-1. The antibody or its fragment can be obtained by in vitro culture or injection into the animals of cells producing the antibody or its fragment. The antibody or its fragment can be obtained from the ascites of animals in which the cells producing the antibody or its fragment are intraperitoneally injected. The antibody or its fragment can be purified from the culture supernatant or ascites by ion exchange chromatography or affinity column chromatography.

The invention also provides the hybridoma cell producing MD-3 antibody, and in an embodiment, the hybridoma cell is the cell of receipt number of KCLRF-BP-00264.

The present invention also relates to a pharmaceutical composition for the prevention and/or treatment of T cell-mediated immune disorders, such as transplantation rejection, graft-versus-host disease, autoimmune disease, and the like. The pharmaceutical composition may comprise an immunosuppressive agent selected from the group consisting of a mouse anti-human ICAM-1 monoclonal antibody, designated MD-3 (produced by a hybridoma cell of receipt number of KCLRF-BP-00264), fragments of MD-3, or a chimeric or humanized form of MD-3. Administration of the antibody or its fragment according to the invention can be carried out using any of the accepted modes of administration of pharmaceutical compositions.

Further, the present invention also relates to a method for the prevention and/or treatment of T cell-mediated immune disorders, such as transplantation rejection, graft-versus-host disease, autoimmune disease, and the like, comprising the step of administering one or more selected from the group consisting of the antibody (e.g., MD-3) or its fragments to a patient in need thereof. The antibody or its fragment may be preferably selected from the group consisting of monoclonal antibodies, and more preferably it is originated from human and animal. The method may additionally comprise the step of identifying the patient in need of treating and/or preventing of the T cell-mediated immune disorders, such as transplantation rejection, graft-versus-host disease, autoimmune disease, and the like, prior to the administration step.

In another embodiment, the present invention provides the antibody (e.g., MD-3) or its fragments for use in treating and/or preventing of the T cell-mediated immune disorders, such as transplantation rejection, graft-versus-host disease, autoimmune disease, and the like; or in preparing a pharmaceutical composition for treating and/or preventing of the T cell-mediated immune disorders, such as transplantation rejection, graft-versus-host disease, autoimmune disease, and the like.

A humanized antibody is an antibody having complementary determining regions (CDRs) from a donor antibody and variable region framework and constant regions from a human antibody. Thus, typically a humanized antibody comprises (i) a light chain comprising three CDRs from a mouse antibody, e.g., MD-3, a variable region framework from a human antibody, and a human constant region, and (ii) a heavy chain comprising three CDRs from a mouse antibody, e.g., MD-3, a variable region framework from a human antibody and a human constant region.

A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies.

The monoclonal antibodies (mAbs) may be of animal (e.g., mouse, rat, hamster or chicken) origin, or they may be genetically engineered. Rodent mAbs are made by standard methods well-known in the art, comprising multiple immunization with ICAM-1 in appropriate adjuvant i.p., i.v., or into the footpad, followed by extraction of spleen or lymph node cells and fusion with a suitable immortalized cell line, and then selection for hybridomas that produce antibody binding to ICAM-1, e.g., see under Examples. Chimeric and humanized mAbs are preferred embodiments of the invention.

Native monoclonal antibodies (mAbs) of the invention may be produced from their hybridomas. Genetically engineered mAbs, e.g., chimeric or humanized mAbs, may be expressed by a variety of art-known methods. For example, genes encoding their light and heavy chain V regions may be synthesized from overlapping oligonucleotides and inserted together with available C regions into expression vectors (e.g., commercially available from Invitrogen) that provide the necessary regulatory regions, e.g., promoters, enhancers, poly A sites, etc. Use of the CMV promoter-enhancer is preferred. The expression vectors may then be transfected using various well-known methods such as lipofection or electroporation into a variety of mammalian cell lines such as CHO or non-producing myelomas including Sp2/0 and NS0, and cells expressing the antibodies were selected by appropriate antibiotic selection.

Once expressed, the mAbs or other antibodies of the invention may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like. Substantially pure antibodies of at least about 90 or 95% homogeneity are preferred, and 98% or 99% or more homogeneity most preferred, for pharmaceutical uses.

In a preferred embodiment, the present invention provides a pharmaceutical formulation comprising the antibodies described herein. That is, the antibodies can be used in the manufacture of a medicament for treatment of disease. Pharmaceutical formulations (i.e., medicaments) of the antibodies contain the mAb in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids, carbohydrates, chelating agents, sugars, and other standard ingredients known to those skilled in the art.

The mAb is typically present at a concentration of 1-100 mg/ml, e.g., 10 mg/ml.

Antibodies of the invention are typically substantially pure from undesired contaminant. This means that the antibody is typically at least about 50% w/w (weight/weight) pure, as well as being substantially free from interfering proteins and contaminants. Preferably the antibodies are at least 90, 95% or 99% w/w pure.

In another preferred embodiment, the invention provides a method of treating a patient with a disease using an anti-ICAM-1 mAb in a pharmaceutical formulation. The mAb prepared in a pharmaceutical formulation can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The mAb can also be injected directly into the site of disease (e.g., a tumor), or encapsulated into carrying agents such as liposomes. The dose given will be sufficient to alleviate the condition being treated ("therapeutically effective dose") and is likely to be 0.1 to 5 mg/kg body weight, for example 1, 2, 3 or 4 mg/kg, but may be as high as 10 mg/kg or even 15 or 20 mg/kg. A fixed unit dose may also be given, for example, 50, 100, 200, 500 or 1000 mg, or the dose may be based on the patient's surface area, e.g., 100 mg/m$^2$.

The mAb can be administered daily, weekly, biweekly, every other week, monthly or at some other interval, depending, e.g. on the half-life of the mAb, for 1 week, 2 weeks, 4 weeks, 8 weeks, 3-6 months or longer. Repeated courses of treatment are also possible, as is chronic administration. A regime of a dosage and intervals of administration that alleviates or at least partially arrests the symptoms of the disease (biochemical, histologic and/or clinical), including its complications and intermediate pathological phenotypes in development of the disease is referred to as a therapeutically effective regime.

The present invention is further explained in more detail with reference to the following examples. These examples, however, should not be interpreted as limiting the scope of the present invention in any manner.

EXAMPLE 1

The Isolation of Hybridoma Cells Capable of Producing Anti-Human ICAM-1 Monoclonal Antibodies Human peripheral blood mononuclear cells were isolated from healthy volunteer by density-gradient centrifugation on Ficoll-Paque (GE Healthcare). To produce ICAM-1/Fc proteins, mRNAs were extracted from phytohemagglutinin (PHA)-activated human peripheral blood mononuclear cells and the cDNA fragments corresponding to the extracellular domains of human ICAM-1 were amplified with the introduction of NheI and EcoRI sites at the 5' and 3' ends, respectively, by polymerase chain reaction (PCR) using the primers as follows: 5' primer GCT AGC GCA ACC TCA GCC TCG CTATGG CTC (SEQ ID NO: 1); 3' primer, GAA TTC ATC TCA TAC CGG GGG GAG AGC AC (SEQ ID NO: 2). To form the fusion construct of human ICAM-1 and human IgG Fc, this fragment was ligated into EcoRI and XhoI-digested pSecTag plasmid (Invitrogen) containing human IgG1 Fc region. The HEK293 cells (ATCC CRL-1573) were transiently transfected with the plasmids, and ICAM-1/Fc proteins were purified form culture supernatants using protein G column.

Balb/c mice (Female, 6-8 weeks, 17-25 g; KOATECH, Korea) were intraperitoneally immunized with 100 μg of ICAM-1/Fc proteins emulsified in complete Freund's adjuvant and then subsequently subjected to twice immunizations with 100 μg of ICAM-1/Fc proteins emulsified in incomplete Freund's adjuvant at two weeks interval. Two weeks later, immunized mice were boosted with 100 μg of ICAM-1/Fc proteins. The spleen of Balb/c mice was removed 3 days after the last administration to prepare the spleen cell suspension. Monoclonal antibodies were produced by fusing the spleen cells of Balb/c immunized with human ICAM-1/Fc with SP2/

0-Ag14 mouse myeloma cells (ATCC CRL-1581) resistant to 9-azaguanine. Cell fusion method followed Koeler and Milstein method (Koeler & Milstein Nature, 1975, 256, 495-497). $10^8$ spleen cells were fused with $10^7$ myeloma cells using 50% polyethylene glycol 4000 (Roche). The cells were washed and resuspended in Dulbeco's modified Eagle's medium (DMEM) containing 20% fetal bovine serum (FBS), 100 μM hypoxanthine, 0.44 μM aminopterin and 16 μM thymidine (FIAT media; Sigma). The cells were introduced to four 96-well plates and cultured at 37° C. in a 5% $CO_2$ incubator.

When colonies were formed after two weeks, the supernatant were screened using human ICAM-1-transfected HEK 293T cells. Both ICAM-1-transfected and wild type HEK293T cells were stained with culture supernatant and cells producing supernatant reactive against ICAM-1-transfected 293T cells but not wild type 293T cells were selected. Cells taken from the positive wells were subcloned 0.5 cell per well by limiting dilution assay (Antibodies: A Laboratory Manual. Edited by ED HARLOW and DAVID LANE; Cold Spring Harbor: Cold Spring Harbor Laboratory. New York. 1988) to produce stable hybridoma clone with high reactivity of antibody.

One hybridoma cell line obtained from this experiment produced IgG1 antibody that bind to both human and monkey antigens and was given the designation MD-3. The hybridoma named for MD-3 was deposited at the Korean Cell Line Research Foundation (KCLRF) located on Cancer Research Institute Seoul National University, College of Medicine, 28 Yongon-dong, Chongno-Gu, Seould, 110-744, Republic of Korea on May 4, 2011, and received as an accession number of KCLRF-BP-00264.

EXAMPLE 2

Mapping of MD-3 Binding Domain of Human ICAM-1

ICAM-1 has a structure composed of five immunoglobulin-like (Ig-like) domains, a transmembrane domain and a cytoplasmic domain (Cell. 1992, 68:71-81). In order to localize the site of MD-3 binding to a particular ICAM-1 Ig-like domain, two kinds of chimeric cDNAs were made that code for human domain 1/murine domains 2-5 including murine transmembrane and cytoplasmic domains (h1m2345) and for human domains 1-2/murine domains 3-5 (h12m345), using human and murine ICAM-1 cDNA clones. The overlapping PCR technique was used to construct these chimeric mutants. The cDNA containing human domain 1 (h1) was first amplified using the primers as follows: 5' primer GAA TTC ATG GCT CCC AGC AGC CCC CGG CCC GCG CT (SEQ ID NO: 3); 3' primer AGG TCT CAG CTC CAC CCG TTC TGG AGT CCA GTA CAC GGT GAG GAA G (SEQ ID NO: 4). Primers for the generation of murine domains 2-5, a transmembrane domain and a cytoplasmic domain (m2345) were as follows: 5' primer, CTG GAC TCC AGA ACG G GTG GAG CTG AGA CCT CTG CCA GCC TGG CAG (SEQ ID NO: 5); 3' primer GGA TCC GGG AGG TGG GGC TTG TCC CTT GAG TTT TAT GGC (SEQ ID NO: 6). These two kinds of cDNA were mixed and re-amplified using SEQ ID NO: 3 and SEQ ID NO: 6 primers and the final product (h1m2345) was cloned in pcDNA3.1 vector. The mutant that encodes h12m345 was also cloned in the way similar to that for h1m2345 using the following primers: 5' primer for h12, GAA TTC ATG GCT CCC AGC AGC CCC CGG CCC GCG CT (SEQ ID NO: 7); 3' primer for h12, GGT AGC TGG AAG ATC AAA GGT CTG GAG CTG GTA GGG GGC CGA GGT (SEQ ID NO: 8); 5' primer for m345, CAG CTC CAG ACC TTT GAT CTT CCA GCT ACC ATC CCA AAG CTC GAC ACC (SEQ ID NO: 9); 3' primer for m345, GGA TCC GGG AGG TGG GGC TTG TCC CTT GAG TTT TAT GGC (SEQ ID NO: 10).

Figure 1:
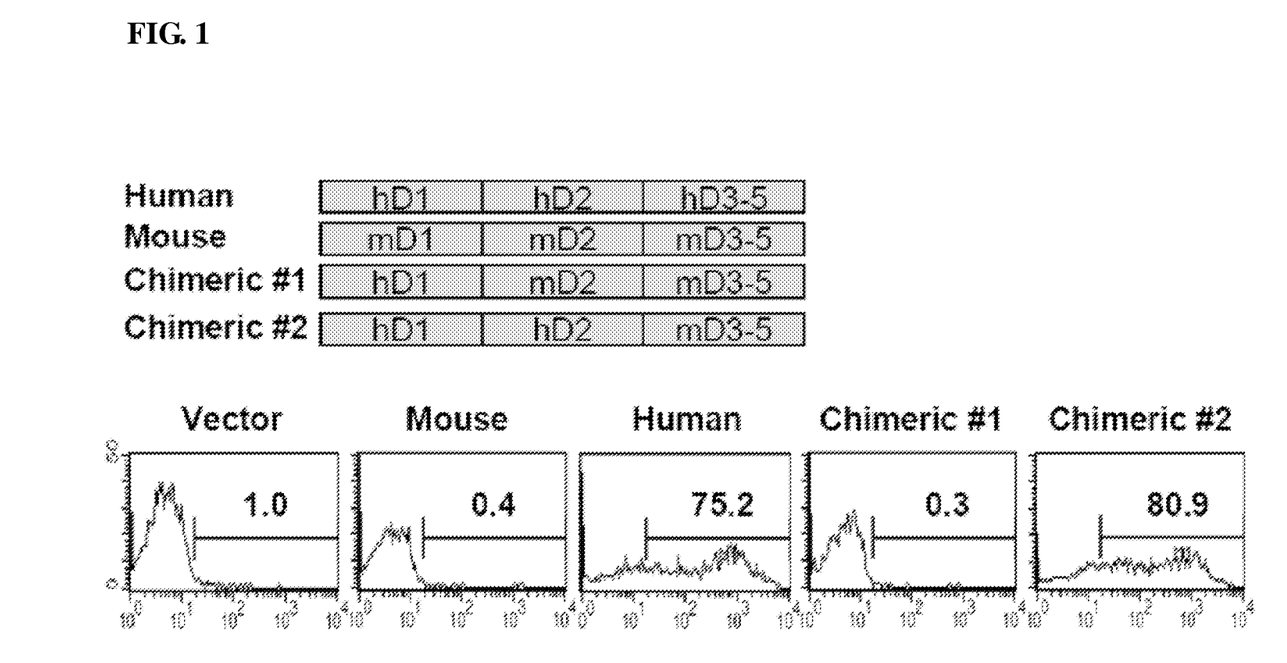
FIG. 1 shows a photograph of the reactivity of MD-3 monoclonal antibody on the HEK293T cells transfected with genes of human ICAM-1, mouse ICAM-1, and two types of chimeric mutants (h1m2345 and h12m345) composed of each domain from human and mouse ICAM-1

The entire construct were sequenced to confirm that the corrected junctions had been obtained and then plasmid DNA were transfected to HEK293T cells using calcium phosphate precipitation method. After incubation of HEK293T cells with coprecipitates of calcium phosphate and plasmid DNA for 16-20 hrs, media were replaced with 10 ml of fresh solution and the cells were incubated for another 24 hours. Then, transfectant was stained with MD-3 antibody in ice. After incubation for 30 min, cells were washed three times in phosphate buffered saline (PBS) with 5% fetal calf serum and 0.1% azide and incubated for 30 min with FITC-conjugated goat anti-mouse Ig antibody ($2^{nd}$ Ab). After a further three washes, flow cytometric analysis was performed to test for their ability to react with each antibody (FIG. 1). As the negative control, cells transfected with vector only were used. As shown in FIG. 1, full human ICAM-1 transfectant was positively stained with MD-3 antibody, whereas it was not reactive with full mouse ICAM-1 transfectant, indicating MD-3 antibody is not cross-reactive with mouse ICAM-1. In the case of chimeric mutants, MD-3 antibody reacted only with mutant containing domain 2 of human ICAM-1 (h12m345), indicating that MD-3 antibody is specific for epitope on domain 2.

EXAMPLE 3

Figure 2:
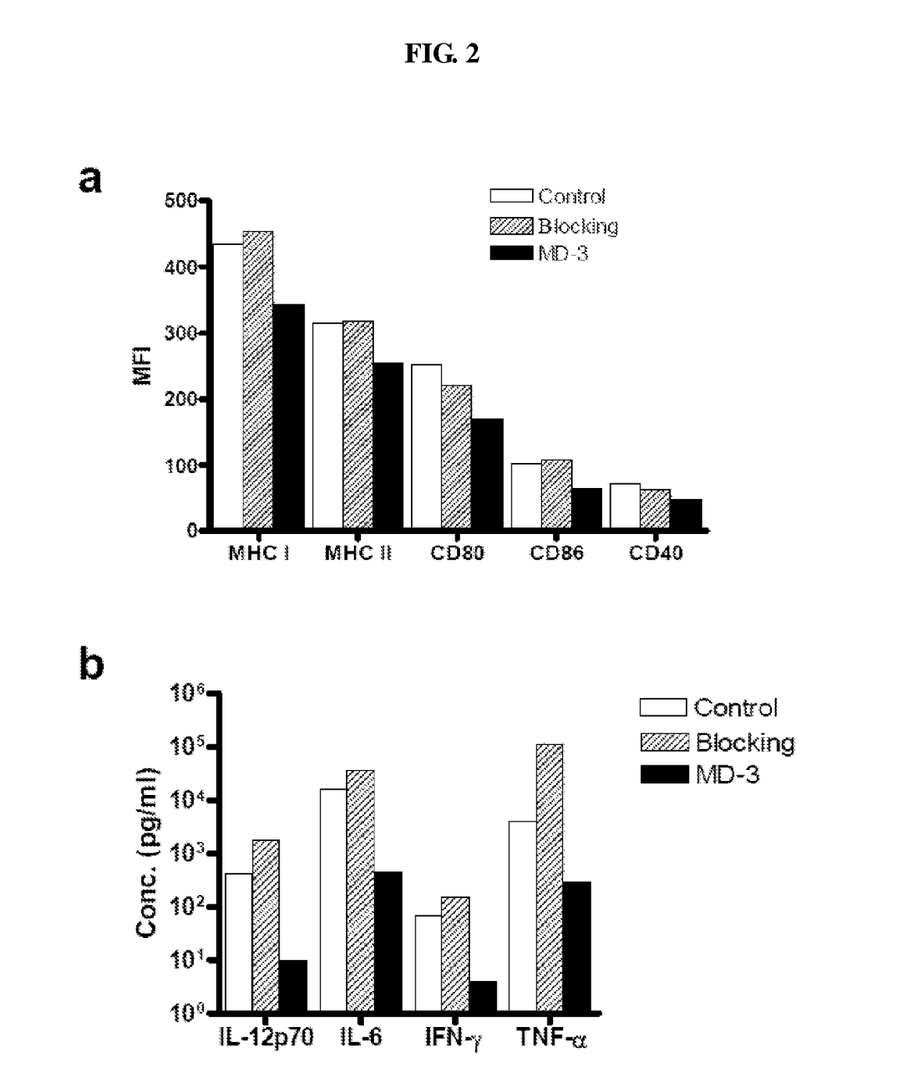
FIG. 2 shows the expression level of various molecules on the surface of dendritic cells and cytokine concentration in the culture media of dendritic cells after treatment of control, blocking, and MD-3 antibodies.
Figure 5:
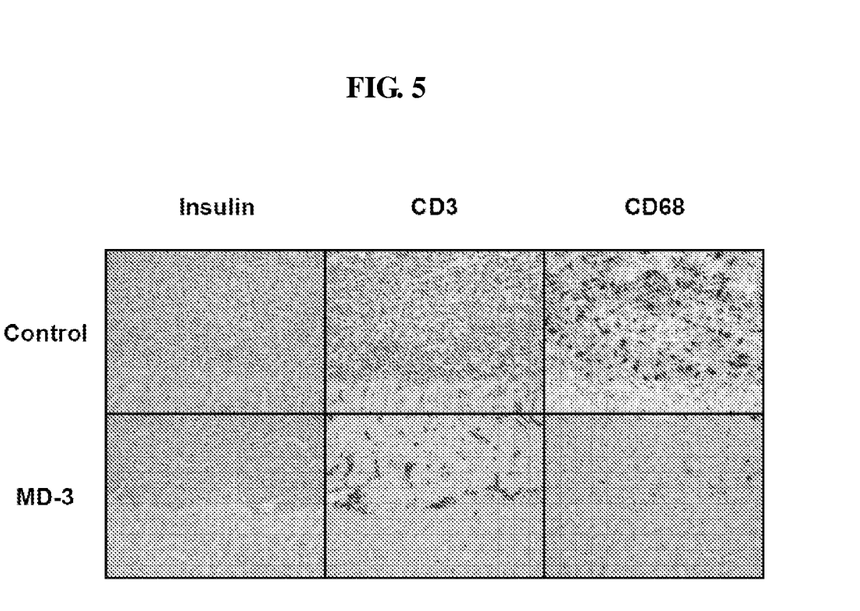
FIG. 5 shows the photograph of immunohistochemical staining for insulin, human CD3, and human CD68 in islet-grafted kidneys extracted from each humanized mouse.

Inhibitory Effect of MD-3 Antibody in the Differentiation of Monocyte-Derived Dendritic Cells Peripheral blood mononuclear cells were isolated from healthy donor blood by Ficoll-hypaque density-gradient centrifugation. After washing twice with PBS, cells were re-suspended in MACS buffer (Milteny-Biotech) at the concentration of $1\times10^8$ cells/ml and then incubated with anti-CD14 magnetic bead (20 μl/$10^7$ cells; Miltenyi Biotec, Bergisch Gladbach, Germany) in ice for 15 minutes, followed by magnetic separation using MACS (Milteny-Biotech). Purified $CD14^+$ monocytes were resuspended in RPMI (Invitrogen) with 10%(v/v) FBS and were cultured for 6 days with granulocytes-macrophage colony stimulating factor (GM-CSF, 1000 U/ml) and IL-4 (1000 U/ml). The culture was supplemented with MD-3 or isotype matched control antibody (10 mg/ml,) on day 0 and day 3 and LPS was added to the culture medium on day 6. One day later, cultured cells were harvested and expression of MHC class I, MHC class II, CD80, CD86, and CD40 was assessed as the mean fluorescence intensity (MFI) by flow cytometry (FIG. 2a). ELISA was also done to measure the amount of IL-12p70, IL-6, IFN-γ and TNF-α in culture media (FIG. 2b). When $CD14^+$ monocytes were cultured in the presence of GM-CSF and IL-4, they are able to differentiate into the immature DCs and LPS treatment induces the maturation of immature DCs, resulting in the up-regulation of the surface expression of MHC and co-stimulatory molecules and cytokine production. However, pretreatment of MD-3 antibody prior to LPS stimulation significantly suppressed the up-regulation of surface molecule expression and cytokine production in the DCs, while it was not case in the DCs treated with blocking antibody (FIG. 5). Thus, these results indicate that MD-3 antibody is able to inhibit the maturation of monocyte-derived DCs.

EXAMPLE 4

Generation of Humanized Mice

To investigate the in vivo effect of anti-ICAM-1 antibodies, humanized mice were generated by engraftment of human hematopoietic stem cells in immunodeficient mice according the procedure by Ito, M. et al., Blood. 2002, 100:3175-82.

Figure 3A:
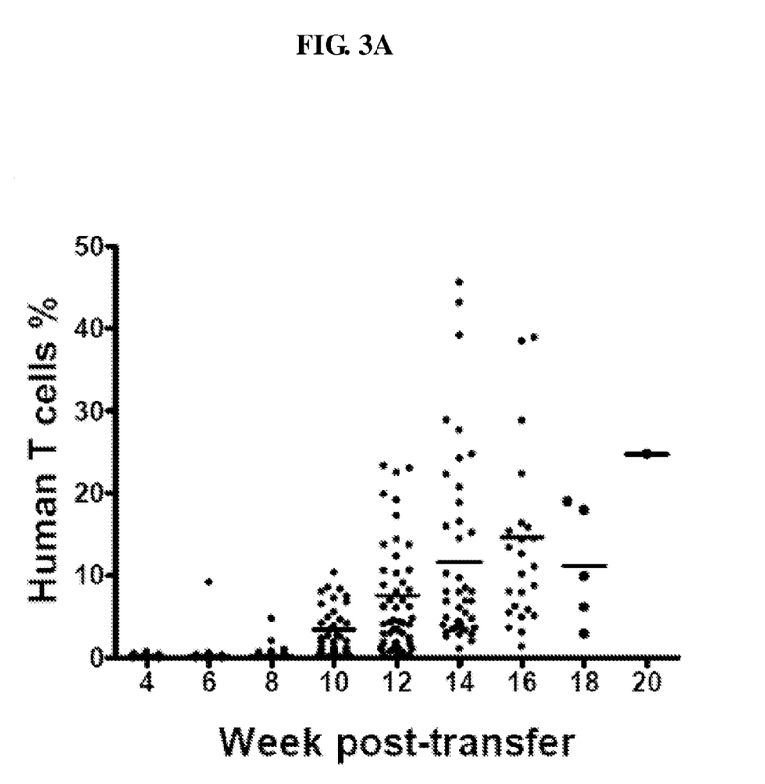
FIGS. 3A and 3B show the repopulation kinetics of human T cells in peripheral blood (3A) and each human leukocyte subset in spleen of humanized mice (3B).
Figure 3B:
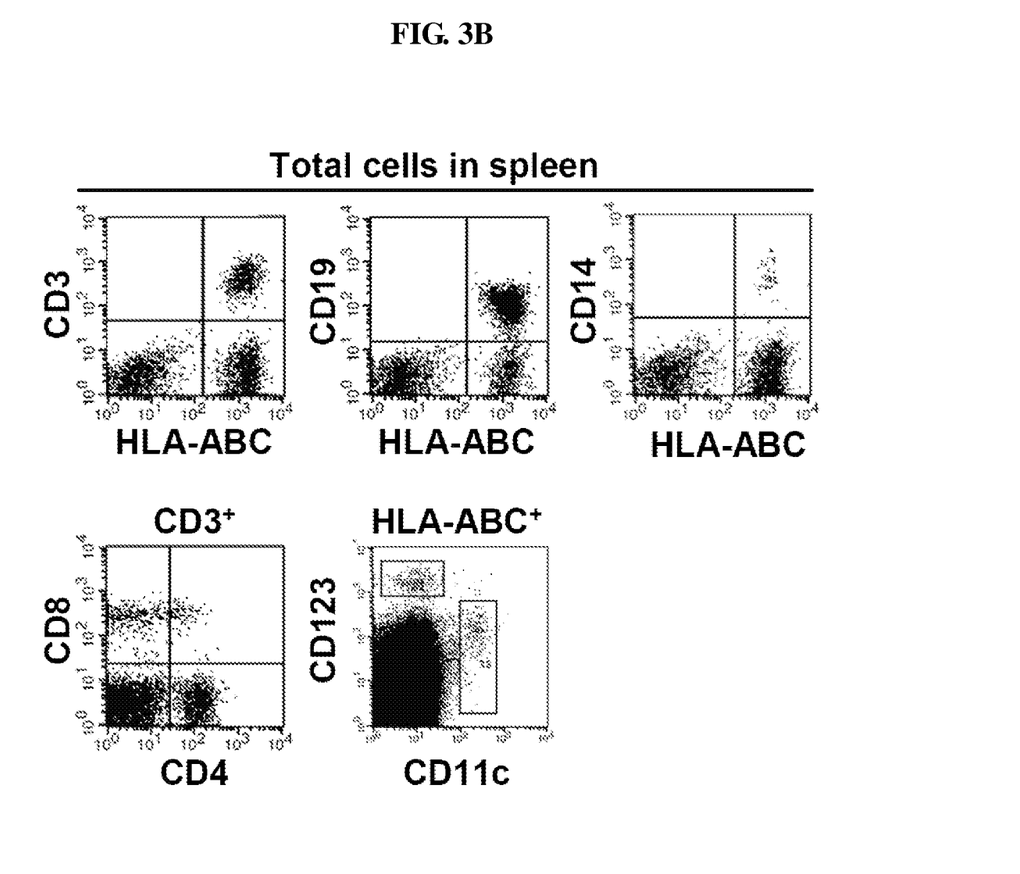

Umbilical cord blood cells were collected during normal full-term delivers and mononuclear cells were separated by Ficoll-hypaque centrifugation. Separated mononuclear cell were suspended at $3.3 \times 10^8$ cells/ml in PBS containing 5% FBS and 2 mM EDTA and incubated in ice for 30 minutes with Fc blocking antibody (Milteny-Biotech), followed by incubation in ice for 30 minutes with anti-CD34 magnetic beads (Milteny-Biotech). After twice washing, bead-attached cells were collected by magnetic separation using MACS. After two rounds of magnetic separation, purity was evaluated by flow cytometry and no less than 95% of the collected cells were CD34$^+$. 8- to 12-week-old NOD.SCID/$\gamma c^{null}$ mice (Central Institute for Experimental Animals, Japan) were irradiated with 240 cGy using cobalt radiation source and 1 day later $1 \times 10^5$ CD34$^+$ cells were injected into the each mouse through the tail vein. Peripheral blood was taken from the retro-orbital venous plexus sequentially between weeks 4 and 20 after transplantation and stained with anti-human CD45 and anti-human CD3 antibodies (BD Biosciences) for flow cytometry. FIG. 3A shows the kinetics of human CD3$^+$T cells repopulating the peripheral blood of mice at the indicated weeks after cell transplantation. Human T cells appeared at 8 weeks after cord blood cell transplantation and then rapidly increased. Moreover, human CD4$^+$ T cells, CD8$^+$ T cells, CD19$^+$ B cells, CD14$^+$ monocytes, CD11c$^+$ conventional DCs, and CD123$^+$ plasmacytoid DCs were identified in the spleens of humanized mice (FIG. 3B).

EXAMPLE 5

Figure 4:
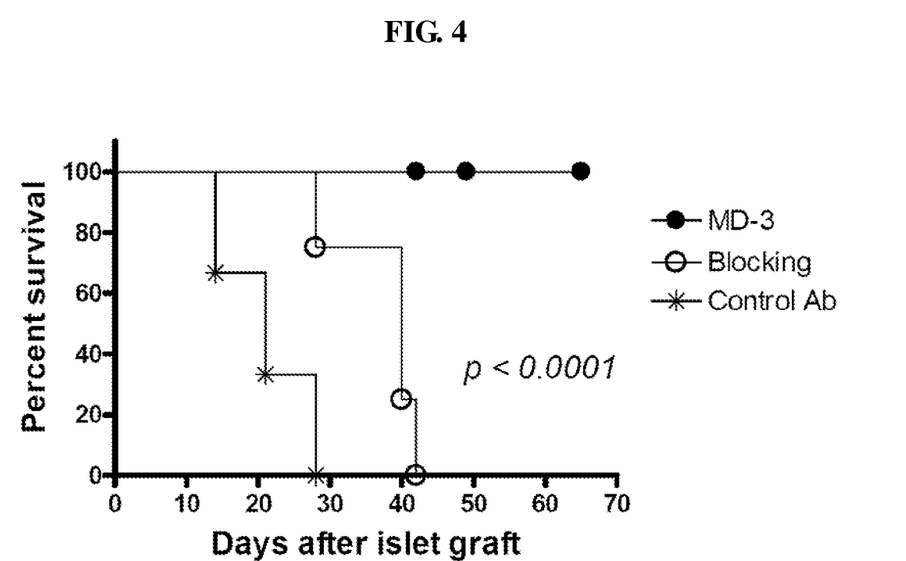
FIG. 4 shows the survival curve of porcine islets grafted under the kidney capsule of humanized mice that received control, blocking, or MD-3 antibodies prior to islet transplantation.

Suppression of Transplantation Rejection Via In Vivo Administration of MD-3 Antibody in Porcine Islet Graft Model In order to demonstrate the effect of MD-3 antibody in suppressing the transplantation rejection, islet xenograft model was used. To obtain porcine pancreatic islets, a total pancreatectomy was performed without warm ischemia time, and islet isolation was performed using the modified Ricordi method, as previously described (Cell Transplant 2010, 19:299-311). Purified islets were cultured overnight in Medium 199 (Gibco, BRL, Life Technologies Ltd, Paisley, Scotland, UK) supplemented with 10% porcine serum, 10 mM nicotinamide (Sigma), and 1% penicillin-streptomycin at 37° C., and then under the kidney capsule of humanized mice. Peripheral blood was sampled weekly from the retro-orbital sinus to monitor blood glucose levels using a portable glucometer (Accu-Chek, Roche Diagnostics, Seoul, South Korea), and porcine C-peptide levels in serum were determined by radioimmunoassay (Linco, St. Charles, Mo., USA). A successful engraft was defined as porcine C-peptide>0.5 ng/ml. Graft rejection was defined as the first day of C-peptide<0.1 ng/ml and confirmed by histological analysis of the grafts. In control group, median graft survival time was 21 days, and the administration of anti-ICAM-1 blocking antibody, R6-5-D6, prolonged the median survival time up to 40 days (FIG. 4). However, grafted islets were eventually rejected in both groups. In contrast, MD-3-treated mice showed no evidence of graft rejection throughout the follow-up period.

Mice were sacrificed at 42 days post-islet transplantation or when they showed a morbid condition, and nephrectomy specimen was analyzed histologically for evidence of graft rejection. Nephrectomy specimen from each mouse was fixed in 10% neural formalin, embedded in paraffin and then serially sectioned in 4 µm thickness. For immunohistochemistry, tissue sections were dewaxed in xylene, rehydrated using a graded alcohol series, and incubated in an endogenous peroxide-blocking solution for 5 minutes. Antigen retrieval was performed by incubating the sections in 6 mM citrate buffer at 99° C. for 20 minutes using the Leica Bond Max system (Leica, Wetzlar, Germany), and non-specific staining was prevented by treating the tissue sections with rabbit serum (1% in PBS) for 30 minutes. Anti-human insulin (DAKO, Carpinteria, Calif., USA), CD3 (F7.2.38; DAKO), CD20 (L26; DAKO), and CD68 (PG-M1; DAKO) antibodies were applied for 30 minutes, and antibody binding was detected using a VECTASTAIN Elite ABC kit (PK6101; Vector Laboratories, Burlingame, Calif., USA). As can be seen in FIG. 5, insulin-positive islet cells were completely destroyed and replaced by predominant infiltrates of CD3$^+$ T cells and CD68$^+$ macrophages in the control group. In the MD-3 treated group, however, large nests of insulin-positive islet cells were clearly seen with negligible infiltration of mononuclear cells in the peri-islet area.

Figure 6:
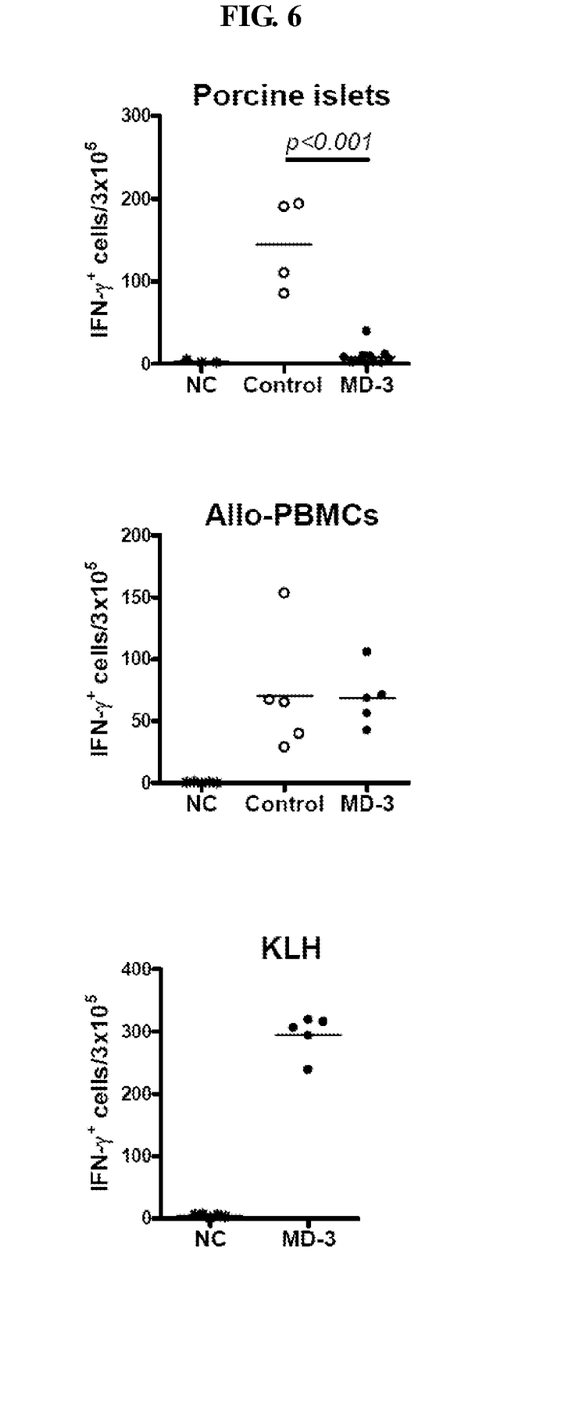
FIG. 6 shows the summarized results of ELISPOT assay to evaluate T cell response against grafted porcine islets, human allo-blood mononuclear cells (allo-PBMCs), and keyhole limpet haemocyanin (KLH)

To address whether the lack of an immune response in MD-3-treated mice was either antigen-specific tolerance or generalized immunosuppression, we compared the numbers of grafted islet-specific and allo-specific T cells in these mice. For this, the frequencies of IL-2 or IFN-γ-secreting antigen-specific T cells in spleens of humanized mice were measured using an ELISPOT kit purchased from Mabtech (Nacka Strand, Sweden). Anti-IL-2 or IFN-γ capture antibody-coated plates were washed four times with sterile phosphate buffered saline (PBS; 200 µl/well) and blocked for 30 minutes with 10% human serum-supplemented RPMI1640 media at room temperature. After removing the media, $3 \times 10^5$ splenocytes from the humanized mice were cultured with $5 \times 10^4$ porcine islet cells in RPMI1640 media supplemented with 10% human serum for 40 h at 37° C. in a 5% CO$_2$ incubator. To evaluate antigen-specific T cell tolerance, keyhole limpet haemocyanin (KLH; 0.1 mg/ml) or T cell-depleted γ-irradiated human peripheral blood mononuclear cells (PBMCs; $7 \times 10^5$/well) pooled from three volunteers were also used as stimulators. As a negative control (NC), splenocytes from humanized mice that did not undergo islet transplantation were stimulated with porcine islets and used for anti-islet response. In contrast, splenocytes from engrafted mice cultured in the absence of stimulating antigen were used for anti-allo-PBMCs and anti-KLH responses. After the 40-hour culture, cells were removed, and the plates were washed five times with PBS (200 µl/well). Alkaline phosphatase-conjugated detecting antibody diluted at 1:200 or 1:1,000 for IL-2 or IFN-γ, respectively, in 100 µl PBS containing 0.5% fetal bovine serum were then added and incubated for 2 hours at room temperature. The plates were washed five times with PBS, and 100 µl of BCIP/NBP substrate was added. Color development was stopped by washing with tap water. The resulting spots were counted on a computer-assisted AID EliSpot Reader System (AID, Strassberg, Germany). When total splenocytes from control mice were stimulated with porcine islets, significant numbers of IL-2- and IFN-γ-secreting T cells were detected (FIG. 6, left). In contrast, IL-2- and IFN-γ-secreting T cells were not detected in MD-3-treated mice, indicating the complete suppression of T cell responses to xenograft antigens. In this system, however, T cells response to human allo-PBMCs was comparable to that of controls (FIG. 6, middle). These data suggest that the unresponsiveness of the T cells reflected the tolerance induction, specific for porcine islet antigens. This induction of antigen-specific T cell tolerance was further evidenced by an in vivo challenge with unrelated antigens. At day 28 post-transplantation, when MD-3 was completely cleared out, mice were immunized with soluble KLH antigen. Two weeks later, numbers of KLH-specific T cells were evaluated in an ELISPOT assay. As shown in FIG. 6 (right), T cells obtained from MD-3-treated mice showed robust response against KLH in terms of the numbers of cells producing IFN-γ and IL-2. These data suggest that the administration of MD-3 induced T cell tolerance specific against graft islet antigens.

What is claimed is:

1. A monoclonal antibody designated MD-3 produced by the hybridoma cell deposited as accession number of KCLRF-BP-00264 or an antigen-binding fragment of the monoclonal antibody, wherein the monoclonal antibody and the antigen-binding fragment bind to domain 2 of ICAM-1.

2. A monoclonal antibody or an antigen-binding fragment of the monoclonal antibody binding to human ICAM-1, the monoclonal antibody comprising a heavy chain and a light chain, the heavy chain comprising three complementary determining regions (CDRs) from the heavy chain of an antibody produced by the hybridoma cell deposited as accession number of KCLRF-BP-00264 and the light chain comprising three CDRs from the light chain of an antibody produced by the hybridoma cell deposited as accession number of KCLRF-BP-00264, wherein the monoclonal antibody and the antigen-binding fragment bind to domain 2 of ICAM-1.

3. A chimeric or humanized form of a monoclonal antibody or an antigen-binding fragment of the monoclonal antibody, the monoclonal antibody and the antigen-binding fragment binding to domain 2 of human ICAM-1, wherein the monoclonal antibody comprises a heavy chain and a light chain, the heavy chain comprising three complementary determining regions (CDRs) from the heavy chain of an antibody produced by the hybridoma cell deposited as accession number of KCLRF-BP-00264 and the light chain comprising three CDRs from the light chain of an antibody produced by the hybridoma cell deposited as accession number of KCLRF-BP-00264.

4. A hybridoma cell deposited as accession number of KCLRF-BP-00264.

5. A pharmaceutical composition comprising the monoclonal antibody or the antigen-binding fragment of claim 1.

6. The pharmaceutical composition according to claim 5, wherein the monoclonal antibody or the antigen-binding fragment is in an isolated form.

7. A chimeric or humanized form of a monoclonal antibody designated MD-3 produced by the hybridoma cell deposited as accession number of KCLRF-BP-00264 or a chimeric or humanized form of an antigen-binding fragment of the monoclonal antibody, wherein the monoclonal antibody and the antigen-binding fragment bind to domain 2 of ICAM-1.

8. A method for treating T cell-mediated immune disorders, the method comprising administering to a patient in need the monoclonal antibody or the antigen-binding fragment according to claim 1 as an active ingredient.

9. The method according to claim 8, wherein one of the T cell-mediated immune disorders is a transplantation rejection, a graft-versus-host disease, or an autoimmune disease.

10. The method of claim 8, wherein the monoclonal antibody or the antigen-binding fragment is administered parenterally.

11. A pharmaceutical composition comprising the monoclonal antibody or the antigen-binding fragment of claim 2.

12. A pharmaceutical composition comprising the chimeric or humanized form of the monoclonal antibody or the antigen-binding fragment according to claim 3, wherein the chimeric or humanized form of the monoclonal antibody or the antigen-binding fragment is in an isolated form.

13. A pharmaceutical composition comprising the chimeric or humanized form of the monoclonal antibody or the antigen-binding fragment according to claim 7, wherein the chimeric or humanized form of the monoclonal antibody or the antigen-binding fragment is in an isolated form.

14. A method for treating T cell-mediated immune disorders, the method comprising administering to a patient in need the chimeric or humanized form of the monoclonal antibody or the antigen-binding fragment according to claim 7 as an active ingredient.

15. The method according to claim 14, wherein one of the T cell-mediated immune disorders is a transplantation rejection, a graft-versus-host disease, or an autoimmune disease.

16. The method of claim 14, wherein the chimeric or humanized form of the monoclonal antibody or the antigen-binding fragment is administered parenterally.

17. A method for treating T cell-mediated immune disorders, the method comprising administering to a patient in need the monoclonal antibody or the antigen-binding fragment according to claim 2 as an active ingredient.

18. The method according to claim 17, wherein one of the T cell-mediated immune disorders is a transplantation rejection, a graft-versus-host disease, or an autoimmune disease.

19. The method of claim 17, wherein the monoclonal antibody or the antigen-binding fragment is administered parenterally.

20. A method for treating T cell-mediated immune disorders, the method comprising administering to a patient in need the chimeric or humanized form of monoclonal antibody or the antigen-binding fragment according to claim 3 as an active ingredient.

21. The method according to claim 20, wherein one of the T cell-mediated immune disorders is a transplantation rejection, a graft-versus-host disease, or an autoimmune disease.

22. The method of claim 12, wherein the chimeric or humanized form of the monoclonal antibody or the antigen-binding fragment is administered parenterally.

* * * * *

SEQUENCE LISTING

```
<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: 5' primer for amplifying the extracellular
      domains of human ICAM-1

<400> SEQUENCE: 1
gctagcgcaa cctcagcctc gctatggctc                                      30

<210> SEQ ID NO 2
<211> LENGTH: 29
<212> TYPE: DNA
<213> ORGANISM: Artificial Sequence
<220> FEATURE:
<223> OTHER INFORMATION: 3' primer for amplifying the extracellular
      domains of human ICAM-1

<400> SEQUENCE: 2
gaattcatct cataccgggg ggagagcac                                       29

<210> SEQ ID NO 3
<211> LENGTH: 35
<212> TYPE: DNA
<213> ORGANISM: Artificial Sequence
<220> FEATURE:
<223> OTHER INFORMATION: 5' primer for amplifying human ICAM-1 domain 1
      (h1)

<400> SEQUENCE: 3
gaattcatgg ctcccagcag cccccggccc gcgct                                35

<210> SEQ ID NO 4
<211> LENGTH: 46
<212> TYPE: DNA
<213> ORGANISM: Artificial Sequence
<220> FEATURE:
<223> OTHER INFORMATION: 3' primer for amplifying human ICAM-1 domain 1
      (h1)

<400> SEQUENCE: 4
aggtctcagc tccacccgtt ctggagtcca gtacacggtg aggaag                    46

<210> SEQ ID NO 5
<211> LENGTH: 46
<212> TYPE: DNA
<213> ORGANISM: Artificial Sequence
<220> FEATURE:
<223> OTHER INFORMATION: 5' primer for amplifying murine ICAM-1 domains
      2-5, a transmembrane domain and a cytoplasmic domain (m2345)

<400> SEQUENCE: 5
ctggactcca gaacgggtgg agctgagacc tctgccagcc tggcag                    46
```

<210> SEQ ID NO 6
<211> LENGTH: 39
<212> TYPE: DNA
<213> ORGANISM: Artificial Sequence
<220> FEATURE:
<223> OTHER INFORMATION: 3' primer for amplifying murine ICAM-1 domains
      2-5, a transmembrane domain and a cytoplasmic domain (m2345)

<400> SEQUENCE: 6
ggatccggga ggtggggctt gtcccttgag ttttatggc                    39

<210> SEQ ID NO 7
<211> LENGTH: 35
<212> TYPE: DNA
<213> ORGANISM: Artificial Sequence
<220> FEATURE:
<223> OTHER INFORMATION: 5' primer for amplifying human ICAM-1 domains
      1-2 (h12)

<400> SEQUENCE: 7
gaattcatgg ctcccagcag ccccggccc gcgct                         35

<210> SEQ ID NO 8
<211> LENGTH: 45
<212> TYPE: DNA
<213> ORGANISM: Artificial Sequence
<220> FEATURE:
<223> OTHER INFORMATION: 3' primer for amplifying human ICAM-1 domains
      1-2 (h12)

<400> SEQUENCE: 8
ggtagctgga agatcaaagg tctggagctg gtaggggggcc gaggt             45

<210> SEQ ID NO 9
<211> LENGTH: 48
<212> TYPE: DNA
<213> ORGANISM: Artificial Sequence
<220> FEATURE:
<223> OTHER INFORMATION: 5' primer for amplifying murine ICAM-1 domains
      3-5 (m345)

<400> SEQUENCE: 9
cagctccaga cctttgatct tccagctacc atcccaaagc tcgacacc           48

<210> SEQ ID NO 10
<211> LENGTH: 39
<212> TYPE: DNA
<213> ORGANISM: Artificial Sequence
<220> FEATURE:
<223> OTHER INFORMATION: 3' primer for amplifying murine ICAM-1 domains
      3-5 (m345)

<400> SEQUENCE: 10
ggatccggga ggtggggctt gtcccttgag ttttatggc                    39